(12) United States Patent
Serizawa et al.

(10) Patent No.: US 11,510,914 B2
(45) Date of Patent: Nov. 29, 2022

(54) AGENT FOR INHIBITING RISE IN INTRANEURONAL CALCIUM CONCENTRATION

(71) Applicant: Toray Industries, Inc., Tokyo (JP)

(72) Inventors: Kanako Serizawa, Kamakura (JP); Kazumi Nishimura, Kamakura (JP); Tomohiko Suzuki, Kamakura (JP); Tatsuya Nishi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 75 days.

(21) Appl. No.: 17/040,458

(22) PCT Filed: Mar. 29, 2019

(86) PCT No.: PCT/JP2019/014045
§ 371 (c)(1),
(2) Date: Sep. 22, 2020

(87) PCT Pub. No.: WO2019/189781
PCT Pub. Date: Oct. 3, 2019

(65) Prior Publication Data
US 2021/0023068 A1  Jan. 28, 2021

(30) Foreign Application Priority Data
Mar. 30, 2018  (JP) .............. JP2018-066541

(51) Int. Cl.
A61K 31/454 (2006.01)
A61P 25/00 (2006.01)
A61K 31/4178 (2006.01)
A61K 31/496 (2006.01)

(52) U.S. Cl.
CPC ........ A61K 31/454 (2013.01); A61K 31/4178 (2013.01); A61K 31/496 (2013.01); A61P 25/00 (2018.01)

(58) Field of Classification Search
CPC .................... C07D 401/06; A61K 31/454
See application file for complete search history.

(56) References Cited

U.S. PATENT DOCUMENTS

| 6,906,072 B1 | 6/2005 | Yamamoto et al. |
| 2007/0197594 A1 | 8/2007 | Hayashibe et al. |
| 2018/0065950 A1 | 3/2018 | Arai et al. |

FOREIGN PATENT DOCUMENTS

| RU | 2 230 060 C2 | 6/2004 |
| RU | 2 347 776 C2 | 2/2009 |
| WO | 2013/147160 A1 | 10/2013 |
| WO | 2016/136944 A1 | 9/2016 |

OTHER PUBLICATIONS

Fernyhough et al. Cell Calcium. Feb. 2010 47(2): 130-139.*
Berridge, M. J., "Neuronal Calcium Signaling," *Neuron*, 1998, vol. 21, pp. 13-26.
Pchitskaya, E. et al., "Calcium signaling and molecular mechanisms underlying neurodegenerative diseases," *Cell Calcium*, 2018, vol. 70, pp. 87-94.

(Continued)

*Primary Examiner* — Kamal A Saeed
(74) *Attorney, Agent, or Firm* — DLA Piper LLP (US)

(57) ABSTRACT

A method of inhibiting a rise in intraneuronal calcium concentration includes administering an effective amount of a cyclic amine derivative represented by formula (I) or a pharmacologically acceptable salt thereof to a subject in need thereof:

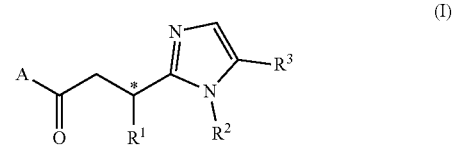

(I)

wherein A represents formula (IIa), (IIb) or (IIc):

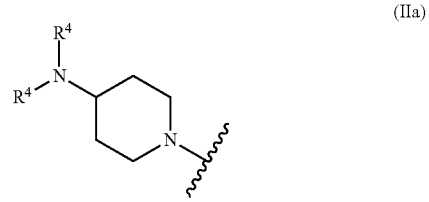

(IIa)

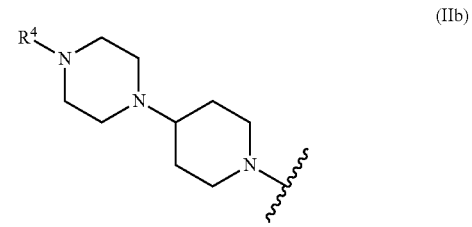

(IIb)

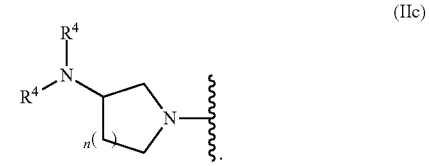

(IIc)

24 Claims, No Drawings

(56) References Cited

OTHER PUBLICATIONS

Fink, K. et al., "Inhibition of neuronal $Ca^{2+}$ influx by gabapentin and subsequent reduction of neurotransmitter release from rat neocortical slices," *British Journal of Pharmacology*, 2000, vol. 130, pp. 900-906.
Russian Official Action dated May 31, 2022, from counterpart Russian Application No. 2020135329 with English translation.
Office Action dated Aug. 29, 2022, of counterpart Taiwanese Patent Application No. 108111163, along with a machine translation.

* cited by examiner

AGENT FOR INHIBITING RISE IN INTRANEURONAL CALCIUM CONCENTRATION

TECHNICAL FIELD

This disclosure relates to an agent for inhibiting a rise in intraneuronal calcium concentration.

BACKGROUND

Intracellular calcium in neurons plays a very important role as a messenger of intracellular signal transduction in regulating cell functions such as differentiation, proliferation, growth, survival, apoptosis, gene transcription, membrane excitation, neurotransmitter release and synaptic plasticity (Berridge, Neuron, 1998, vol. 21, p. 13-26 and Pchitskaya et al., Cell Calcium, 2018, vol. 70, p. 87-94).

The intracellular calcium concentration is kept at several tens to hundreds of nmol/L in a normal state, whereas the intracellular calcium concentration rises to several hundreds of nmol/L to several tens of μmol/L when the cells are variously stimulated. This rise in intracellular calcium concentration causes diverse life responses. After completion of necessary life responses, the intracellular calcium concentration restores its normal level. Thus, for normally exerting the functions of cells, it is essential to strictly control the intracellular concentration of calcium flowing into or out of the cells via various receptors, ion channels and the like.

In neurons, excitatory transmission, which is the important function of the neurons, occurs when the intracellular calcium concentration rises. If the intraneuronal calcium concentration becomes out of strict control due to some cause, an abnormal rise in intraneuronal calcium concentration occurs, consequently causing many nervous diseases and nervous disorders. This abnormal rise in intraneuronal calcium concentration is indicated by, for example, an intraneuronal calcium concentration beyond a normal range, the length of a duration of a rise in intraneuronal calcium concentration beyond a normal range, or the number of rises in intraneuronal calcium concentration per unit time beyond a normal range. For example, epilepsy is considered as a disease caused by abnormal excitation of cerebral neurons, specifically, abnormal increase in the number of rises in intraneuronal calcium concentration per unit time. Gabapentin, a therapeutic agent for epilepsy, is known to bind to a voltage-dependent calcium channel presynaptically present in excitatory neurons, and inhibit excitatory synaptic transmission, thereby exerting antiepileptic action (Fink et al., British Journal of Pharmacology, 2000, vol. 130, p. 900-906). Thus, agents for inhibiting a rise in intraneuronal calcium concentration are useful in the prevention or treatment of various nervous diseases and disorders caused by neuronal hyperexcitability associated with a rise in intraneuronal calcium concentration.

International Publication No. WO 2013/147160 and International Publication No. WO 2016/136944 disclose that cyclic amine derivatives have analgesic action, but neither disclose nor suggest their effects related to the inhibition of a rise in intraneuronal calcium concentration.

It could therefore be helpful to provide an agent for inhibiting a rise in intraneuronal calcium concentration.

SUMMARY

We discovered that the cyclic amine derivative or a pharmacologically acceptable salt thereof has a remarkable inhibitory effect on a rise in intraneuronal calcium concentration.

Specifically, we provide an agent for inhibiting a rise in intraneuronal calcium concentration, comprising a cyclic amine derivative represented by formula (I) or a pharmacologically acceptable salt thereof as an active ingredient:

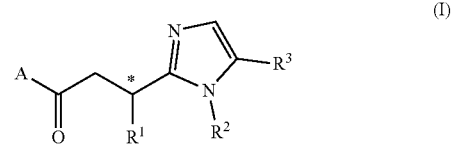

wherein A represents a group represented by formula (IIa), (IIb) or (IIc):

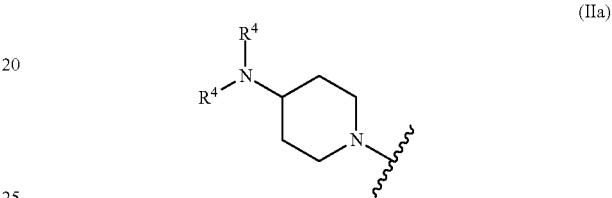

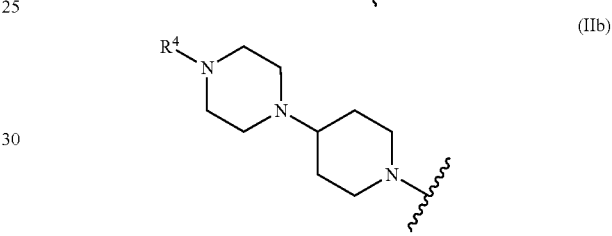

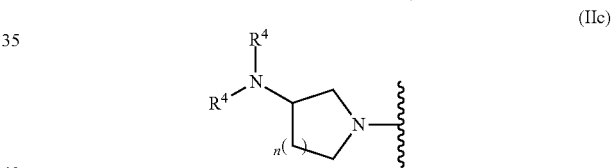

wherein $R^1$ represents a hydroxyl group or a hydrogen atom, $R^2$ represents a methyl group, an ethyl group, a n-propyl group, an isopropyl group, a n-butyl group, a difluoromethyl group or a 2,2,2-trifluoroethyl group, $R^3$ represents a hydrogen atom, a fluorine atom, a bromine atom or a chlorine atom, each $R^4$ independently represents a methyl group or an ethyl group, n represents 1 or 2, and when $R^1$ represents a hydroxyl group, carbon marked with * represents asymmetric carbon.

In the aforementioned cyclic amine derivative, it is preferable that A is the group represented by formula (IIa), in which, $R^2$ is preferably a methyl group, an ethyl group, a n-propyl group, an isopropyl group, a n-butyl group or a 2,2,2-trifluoroethyl group, and $R^3$ is preferably a hydrogen atom or a chlorine atom; when $R^1$ is a hydroxyl group, the stereochemical configuration of the asymmetric carbon marked with * is preferably S. An inhibitory effect on a rise in intraneuronal calcium concentration can be enhanced as mentioned above.

In the aforementioned cyclic amine derivative, it is preferable that A is the group represented by formula (IIb), in which, $R^2$ is preferably a methyl group, an ethyl group, a n-propyl group, an isopropyl group, a n-butyl group or a 2,2,2-trifluoroethyl group, and $R^3$ is preferably a hydrogen atom or a chlorine atom; when $R^1$ is a hydroxyl group, the stereochemical configuration of the asymmetric carbon marked with * is preferably S. An inhibitory effect on a rise in intraneuronal calcium concentration can be enhanced as mentioned above.

In the aforementioned cyclic amine derivative, it is preferable that A is the group represented by formula (IIc), and n is 1 or 2, in which, $R^2$ is preferably a methyl group, an ethyl group, a n-propyl group, an isopropyl group, a n-butyl group or a 2,2,2-trifluoroethyl group, and $R^3$ is preferably a hydrogen atom or a chlorine atom; when $R^1$ is a hydroxyl group, the stereochemical configuration of the asymmetric carbon marked with * is preferably S. An inhibitory effect on a rise in intraneuronal calcium concentration can be enhanced as mentioned above.

In the aforementioned cyclic amine derivative, $R^1$ is preferably a hydrogen atom; in this example, $R^2$ is preferably a methyl group, an ethyl group, a n-propyl group, an isopropyl group, a n-butyl group or a 2,2,2-trifluoroethyl group, and $R^3$ is preferably a hydrogen atom or a chlorine atom. An inhibitory effect on a rise in intraneuronal calcium concentration can be more enhanced as mentioned above.

In the aforementioned cyclic amine derivative, $R^1$ is preferably a hydroxyl group; in this example, $R^2$ is preferably a methyl group, an ethyl group, a n-propyl group, an isopropyl group, a n-butyl group or a 2,2,2-trifluoroethyl group, and $R^3$ is preferably a hydrogen atom or a chlorine atom. The stereochemical configuration of the asymmetric carbon marked with * is preferably S. An inhibitory effect on a rise in intraneuronal calcium concentration can be further enhanced as mentioned above.

We also provide a pharmaceutical composition for treating or preventing a disease related to neuronal hyperexcitability, containing a cyclic amine derivative represented by formula (I) or a pharmacologically acceptable salt thereof, and a pharmacologically acceptable excipient and the like.

We further provide a cyclic amine derivative represented by formula (I) or a pharmacologically acceptable salt thereof for use in treatment or prevention of a disease related to neuronal hyperexcitability.

We still further provide use of a cyclic amine derivative represented by formula (I) or a pharmacologically acceptable salt thereof for treating or preventing a disease related to neuronal hyperexcitability.

We yet further provide use of a cyclic amine derivative represented by formula (I) or a pharmacologically acceptable salt thereof in producing a medicine for treating or preventing a disease related to neuronal hyperexcitability.

We also provide a method of treating or preventing a disease related to neuronal hyperexcitability, which includes administering a therapeutically effective amount of a cyclic amine derivative represented by formula (I) or a pharmacologically acceptable salt thereof to a patient in need of treatment.

We further provide a method of inhibiting a rise in intraneuronal calcium concentration, which includes contacting an effective amount of a cyclic amine derivative represented by formula (I) or a pharmacologically acceptable salt thereof with neurons.

We still further provide a method of inhibiting a rise in intraneuronal calcium concentration, which includes administering an effective amount of a cyclic amine derivative represented by formula (I) or a pharmacologically acceptable salt thereof to a subject in need thereof.

Examples of the aforementioned disease related to neuronal hyperexcitability include, but are not limited to: central nervous diseases such as Alzheimer's disease, Parkinson's disease, Huntington's disease, Creutzfeldt-Jakob disease, amyotrophic lateral sclerosis (ALS), spinocerebellar degeneration, spinocerebellar ataxia, Down syndrome, multiple sclerosis, schizophrenia, depression, mania, anxiety neurosis, obsessive-compulsive disorder, panic disorder, bipolar disorder, corticobasal degeneration, progressive supranuclear palsy, Lewy body dementia, frontotemporal lobar degeneration, mild cognitive impairment which is a pre-lesion of Alzheimer's disease, frontotemporal lobar dementia, epilepsy, alcoholism, drug addiction, anxiety symptoms, unpleasant mental states, dysthymia, cyclothymia, nervous erethism, autism, fainting, addition and loss of sexual desire; central nervous system or peripheral nervous damages such as head trauma, spinal cord injury, cerebral edema, perceptual dysfunction, diabetic neuropathy, autonomic nervous system dysfunction and whiplash; disorders of memory such as senile dementia, cerebrovascular dementia and amnesia, intracerebral hemorrhage, cerebral infarction and sequelae and complications thereof, cerebrovascular disorders such as asymptomatic cerebrovascular disorder, transient ischemic attack, hypertensive encephalopathy and brain-blood barrier disorder, and recurrence or sequelae of cerebrovascular disorders; decline in central functions after cerebrovascular occlusion and disorder or abnormality of brain or kidney circulation autoregulation; metabolic disorder syndromes such as idiopathic normal pressure hydrocephalus, obstructive hydrocephalus and infectious or metabolic encephalopathy; autoimmune diseases such as optic neuromyelitis and limbic encephalitis; oncological diseases such as neuroepithelial tissue tumors (glioma, neuronal tumor and the like), neurilemmal tumors (neurilemoma, neurofibromatosis and the like), meningeal tumors (meningioma and other mesenchymal tumors), sellar tumor and metastatic tumor; sleep disorder; and pruritus.

This description incorporates the contents of Japanese Patent Application No. 2018-066541, which is a priority application for this application.

The cyclic amine derivative or a pharmacologically acceptable salt thereof can inhibit a rise in intraneuronal calcium concentration.

DETAILED DESCRIPTION

The following terms used in the specification are, unless otherwise specified, defined as follows.

It is characterized in that the cyclic amine derivative according to one example is represented by formula (I).

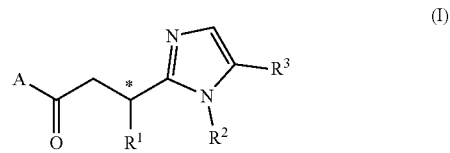

(I)

wherein A represents a group represented by formulae (IIa), (IIb) or (IIc):

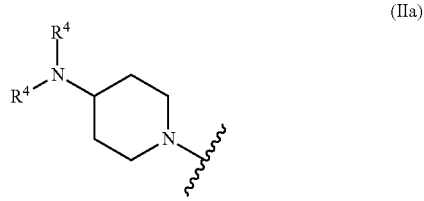

(IIa)

-continued

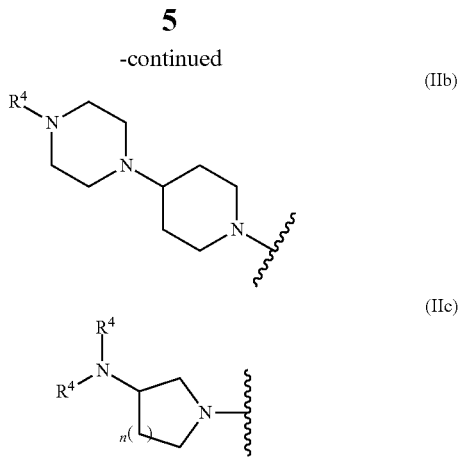

wherein $R^1$ represents a hydroxyl group or a hydrogen atom, $R^2$ represents a methyl group, an ethyl group, a n-propyl group, an isopropyl group, a n-butyl group, a difluoromethyl group or a 2,2,2-trifluoroethyl group, $R^3$ represents a hydrogen atom, a fluorine atom, a bromine atom or a chlorine atom, each $R^4$ independently represents a methyl group or an ethyl group, n represents 1 or 2, and when $R^1$ represents a hydroxyl group, carbon marked with * represents asymmetric carbon.

In the aforementioned cyclic amine derivative, it is preferable that A is the group represented by formula (IIa), in which, $R^2$ is preferably a methyl group, an ethyl group, an isopropyl group, a n-butyl group or a 2,2,2-trifluoroethyl group, and $R^3$ is preferably a hydrogen atom or a chlorine atom. When $R^1$ is a hydroxyl group, the stereochemical configuration of the asymmetric carbon marked with * is preferably S.

In the aforementioned cyclic amine derivative, it is preferable that A is the group represented by formula (IIa), in which, $R^2$ is preferably a n-propyl group, and $R^3$ is preferably a hydrogen atom or a chlorine atom. When $R^1$ is a hydroxyl group, the stereochemical configuration of the asymmetric carbon marked with * is preferably S.

In the aforementioned cyclic amine derivative, it is preferable that A is the group represented by formula (IIb), in which, $R^2$ is preferably a methyl group, an ethyl group, an isopropyl group, a n-butyl group or a 2,2,2-trifluoroethyl group, and $R^3$ is preferably a hydrogen atom or a chlorine atom. When $R^1$ is a hydroxyl group, the stereochemical configuration of the asymmetric carbon marked with * is preferably S.

In the aforementioned cyclic amine derivative, it is preferable that A is the group represented by formula (IIb), in which, $R^2$ is preferably a n-propyl group, and $R^3$ is preferably a hydrogen atom or a chlorine atom. When $R^1$ is a hydroxyl group, the stereochemical configuration of the asymmetric carbon marked with * is preferably S.

In the aforementioned cyclic amine derivative, it is preferable that A is the group represented by formula (IIc), and n is 1 or 2, in which, $R^2$ is preferably a methyl group, an ethyl group, an isopropyl group, a n-butyl group or a 2,2,2-trifluoroethyl group, and $R^3$ is preferably a hydrogen atom or a chlorine atom. When $R^1$ is a hydroxyl group, the stereochemical configuration of the asymmetric carbon marked with * is preferably S.

In the aforementioned cyclic amine derivative, it is preferable that A is the group represented by formula (IIc), and n is 1 or 2, in which, $R^2$ is preferably a n-propyl group, and $R^3$ is preferably a hydrogen atom or a chlorine atom. When $R^1$ is a hydroxyl group, the stereochemical configuration of the asymmetric carbon marked with * is preferably S.

In the aforementioned cyclic amine derivative, $R^1$ is preferably a hydrogen atom, in which, $R^2$ is preferably a methyl group, an ethyl group, an isopropyl group, a n-butyl group or a 2,2,2-trifluoroethyl group, and $R^3$ is preferably a hydrogen atom or a chlorine atom.

In the aforementioned cyclic amine derivative, $R^1$ is preferably a hydrogen atom, in which, $R^2$ is preferably a n-propyl group, and $R^3$ is preferably a hydrogen atom or a chlorine atom.

In the aforementioned cyclic amine derivative, $R^1$ is preferably a hydroxyl group, in which, $R^2$ is preferably a methyl group, an ethyl group, an isopropyl group, a n-butyl group or a 2,2,2-trifluoroethyl group, and $R^3$ is preferably a hydrogen atom or a chlorine atom. The stereochemical configuration of the asymmetric carbon marked with * is preferably S.

In the aforementioned cyclic amine derivative, $R^1$ is preferably a hydroxyl group, in which, $R^2$ is preferably a n-propyl group, and $R^3$ is preferably a hydrogen atom or a chlorine atom. The stereochemical configuration of the asymmetric carbon marked with * is preferably S.

In the cyclic amine derivative according to an another example, A is a group represented by formula (IIa), $R^1$ is a hydrogen atom, $R^2$ is a methyl group, an ethyl group, an isopropyl group, a n-butyl group or a 2,2,2-trifluoroethyl group, $R^3$ is a hydrogen atom, a fluorine atom, a bromine atom or a chlorine atom, and each $R^4$ is independently a methyl group or an ethyl group. In this example, it is preferable that $R^2$ is a methyl group, an ethyl group or a 2,2,2-trifluoroethyl group, and $R^3$ is a hydrogen atom.

In the cyclic amine derivative according to an another example, A is a group represented by formula (IIa), $R^1$ is a hydrogen atom, $R^2$ is a n-propyl group, $R^3$ is a hydrogen atom, a fluorine atom, a bromine atom or a chlorine atom, and each $R^4$ is independently a methyl group or an ethyl group. In this example, it is preferable that $R^3$ is a hydrogen atom.

In the cyclic amine derivative according to an another example, A is a group represented by formula (IIa), $R^1$ is a hydroxyl group, $R^2$ is a methyl group, an ethyl group, an isopropyl group, a n-butyl group or a 2,2,2-trifluoroethyl group, $R^3$ is a hydrogen atom, a fluorine atom, a bromine atom or a chlorine atom, and each $R^4$ is independently a methyl group or an ethyl group. In this example, it is preferable that $R^3$ is a hydrogen atom or a chlorine atom. In this example, it is preferable that $R^2$ is a methyl group, an ethyl group or a 2,2,2-trifluoroethyl group, and $R^3$ is a hydrogen atom. In this example, it is preferable that the stereochemical configuration of the asymmetric carbon marked with * is S.

In the cyclic amine derivative according to an another example, A is a group represented by formula (IIa), $R^1$ is a hydroxyl group, $R^2$ is a n-propyl group, $R^3$ is a hydrogen atom, a fluorine atom, a bromine atom or a chlorine atom, and each $R^4$ is independently a methyl group or an ethyl group. In this example, it is preferable that $R^3$ is a hydrogen atom. In this example, it is preferable that the stereochemical configuration of the asymmetric carbon marked with * is S.

In the cyclic amine derivative according to an another example, A is a group represented by formula (IIb), $R^1$ is a hydroxyl group, $R^2$ is a methyl group, an ethyl group, an isopropyl group, a n-butyl group or a 2,2,2-trifluoroethyl group, $R^3$ is a hydrogen atom, a fluorine atom, a bromine atom or a chlorine atom, and each $R^4$ is independently a methyl group or an ethyl group. In this example, it is preferable that $R^2$ is a methyl group, an ethyl group or a 2,2,2-trifluoroethyl group, and $R^3$ is a hydrogen atom. In this example, it is preferable that the stereochemical configuration of the asymmetric carbon marked with * is S.

In the cyclic amine derivative according to an another example, A is a group represented by formula (IIb), $R^1$ is a hydroxyl group, $R^2$ is a n-propyl group, $R^3$ is a hydrogen atom, a fluorine atom, a bromine atom or a chlorine atom, and each $R^4$ is independently a methyl group or an ethyl group. In this example, it is preferable that $R^3$ is a hydrogen atom. In this example, it is preferable that the stereochemical configuration of the asymmetric carbon marked with * is S.

In the cyclic amine derivative according to an another example, A is a group represented by formula (IIc), n is 1 or 2, $R^1$ is a hydroxyl group, $R^2$ is a methyl group, an ethyl group, an isopropyl group, a n-butyl group or a 2,2,2-trifluoroethyl group, $R^3$ is a hydrogen atom, a fluorine atom, a bromine atom or a chlorine atom, and each $R^4$ is independently a methyl group or an ethyl group. In this example, it is preferable that $R^2$ is a methyl group, an ethyl group or a 2,2,2-trifluoroethyl group, and $R^3$ is a hydrogen atom. In this example, it is preferable that the stereochemical configuration of the asymmetric carbon marked with * is S.

In the cyclic amine derivative according to an another example, A is a group represented by formula (IIc), n is 1 or 2, $R^1$ is a hydroxyl group, $R^2$ is a n-propyl group, $R^3$ is a hydrogen atom, a fluorine atom, a bromine atom or a chlorine atom, and each $R^4$ is independently a methyl group or an ethyl group. In this example, it is preferable that $R^3$ is a hydrogen atom. In this example, it is preferable that the stereochemical configuration of the asymmetric carbon marked with * is S.

In the cyclic amine derivative according to an another example, A is a group represented by formula (IIa), $R^1$ is a hydroxyl group or a hydrogen atom, $R^2$ is a n-propyl group, an isopropyl group or a n-butyl group, $R^3$ is a hydrogen atom, a fluorine atom, a bromine atom or a chlorine atom, and each $R^4$ is independently a methyl group or an ethyl group; when $R^1$ is a hydroxyl group, carbon marked with * represents asymmetric carbon.

In the cyclic amine derivative according to an another example, A is a group represented by formula (IIb), $R^1$ is a hydroxyl group or a hydrogen atom, $R^2$ is a n-propyl group, an isopropyl group or a n-butyl group, $R^3$ is a hydrogen atom, a fluorine atom, a bromine atom or a chlorine atom, and each $R^4$ is independently a methyl group or an ethyl group; when $R^1$ is a hydroxyl group, carbon marked with * represents asymmetric carbon.

In the cyclic amine derivative according to an another example, A is a group represented by formula (IIc), $R^1$ is a hydroxyl group or a hydrogen atom, $R^2$ is a n-propyl group, an isopropyl group or a n-butyl group, $R^3$ is a hydrogen atom, a fluorine atom, a bromine atom or a chlorine atom, each $R^4$ is independently a methyl group or an ethyl group, and n is 1 or 2; when $R^1$ is a hydroxyl group, carbon marked with * represents asymmetric carbon.

Specific examples of a preferable compound as a cyclic amine derivative represented by formula (I) (hereinafter, cyclic amine derivative (I)) will be shown in Tables 1-1, 1-2 and 1-3. However, this disclosure is not limited to these.

TABLE 1-1

Structural formula

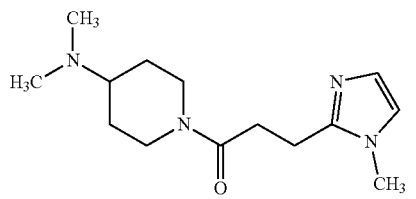 [SMILES: CN(C)C1CCN(C(=O)CCc2nccn2C)CC1]

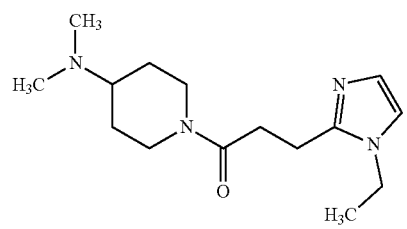

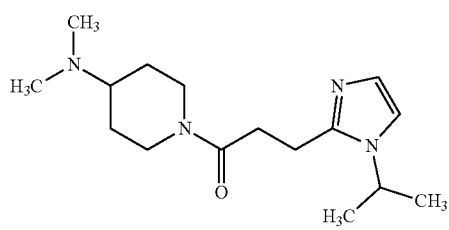 [SMILES: CC(C)n1ccnc1CCC(=O)N1CCC(N(C)C)CC1]

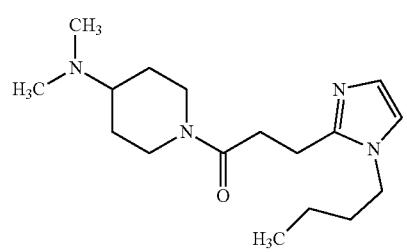

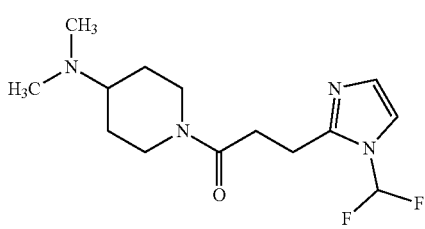 [SMILES: CN(C)C1CCN(C(=O)CCc2nccn2C(F)F)CC1]

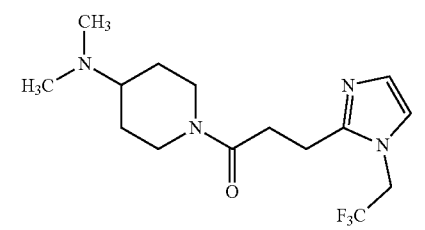 [SMILES: CN(C)C1CCN(C(=O)CCc2nccn2CC(F)(F)F)CC1]

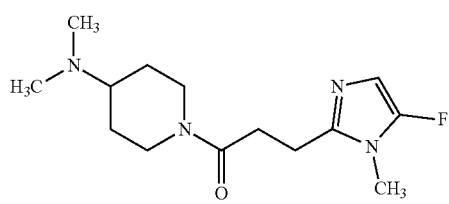 [SMILES: CN(C)C1CCN(C(=O)CCc2ncc(F)n2C)CC1]

TABLE 1-1-continued
Structural formula
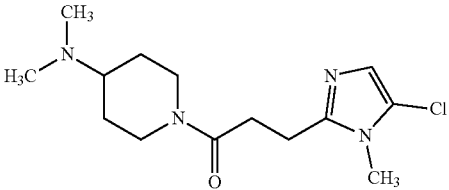 [SMILES: CN(C)C1CCN(C(=O)CCc2ncc(Cl)n2C)CC1]
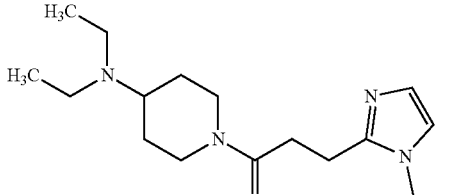
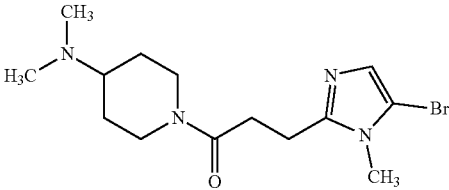
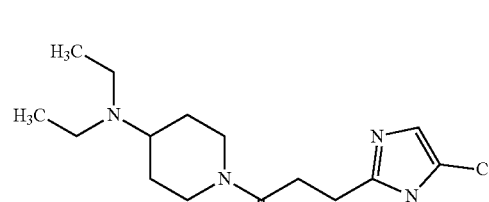
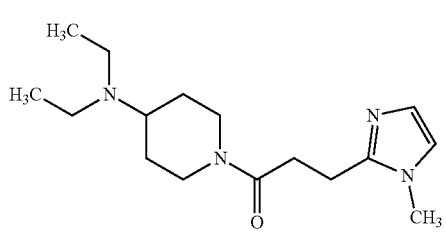 [SMILES: CCN(CC)C1CCN(C(=O)CCc2nccn2C)CC1]
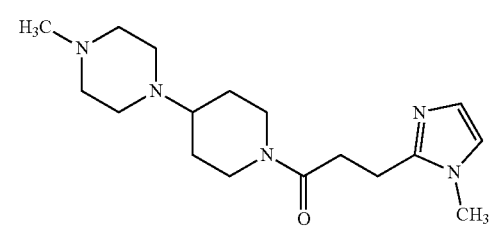
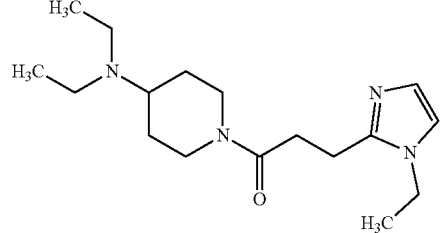 [SMILES: CCN(CC)C1CCN(C(=O)CCc2nccn2CC)CC1]
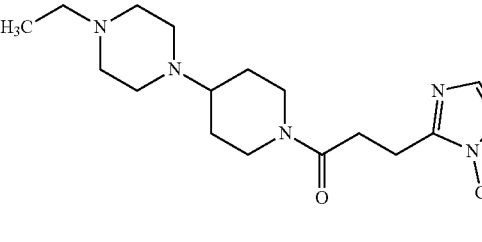
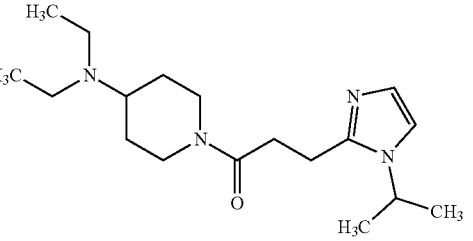
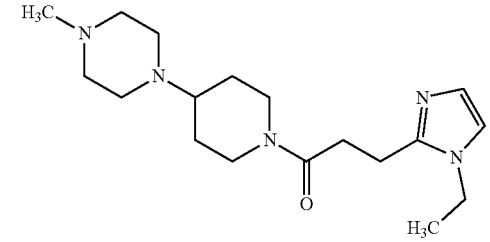 [SMILES: CCn1ccnc1CCC(=O)N1CCC(N2CCN(C)CC2)CC1]
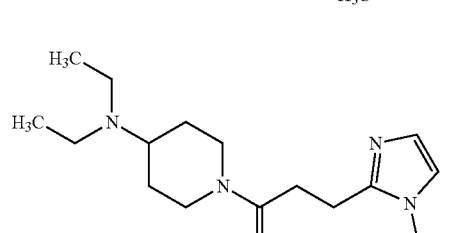
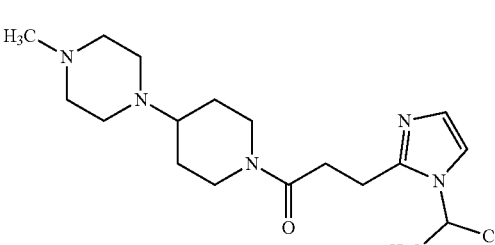
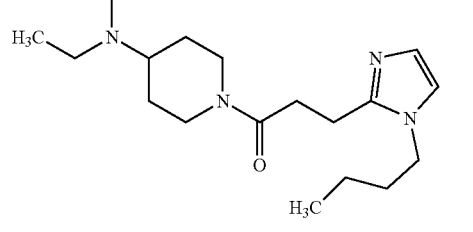

TABLE 1-1-continued

Structural formula (structures shown)

TABLE 1-2

Structural formula (structures shown)

TABLE 1-2-continued

Structural formula (structures shown)

TABLE 1-2-continued

Structural formula (page 13 / 14, chemical structures only)

TABLE 1-2-continued
Structural formula
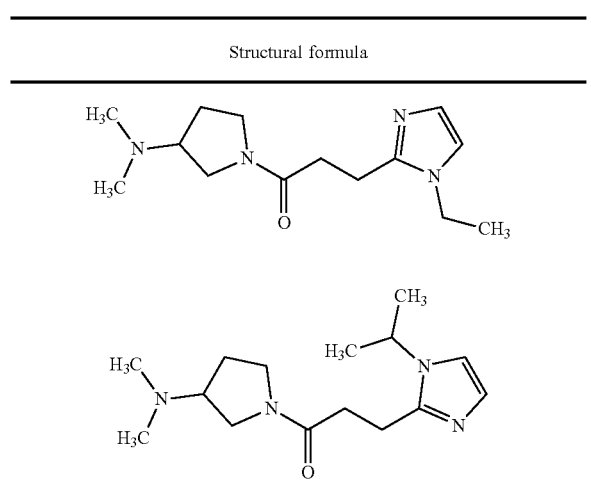
TABLE 1-3
Structural formula
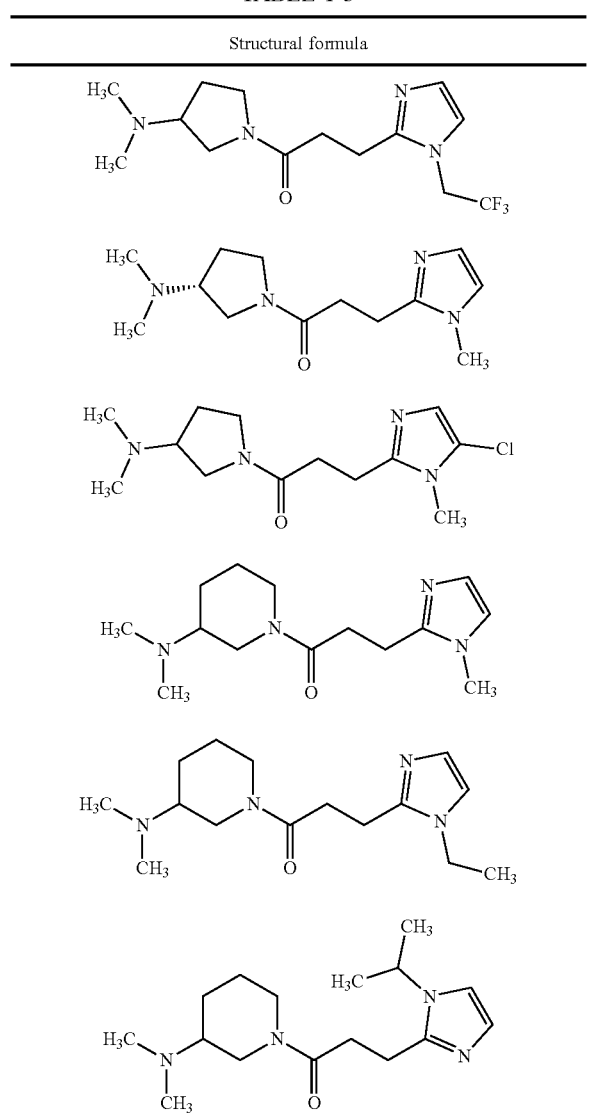
TABLE 1-3-continued
Structural formula
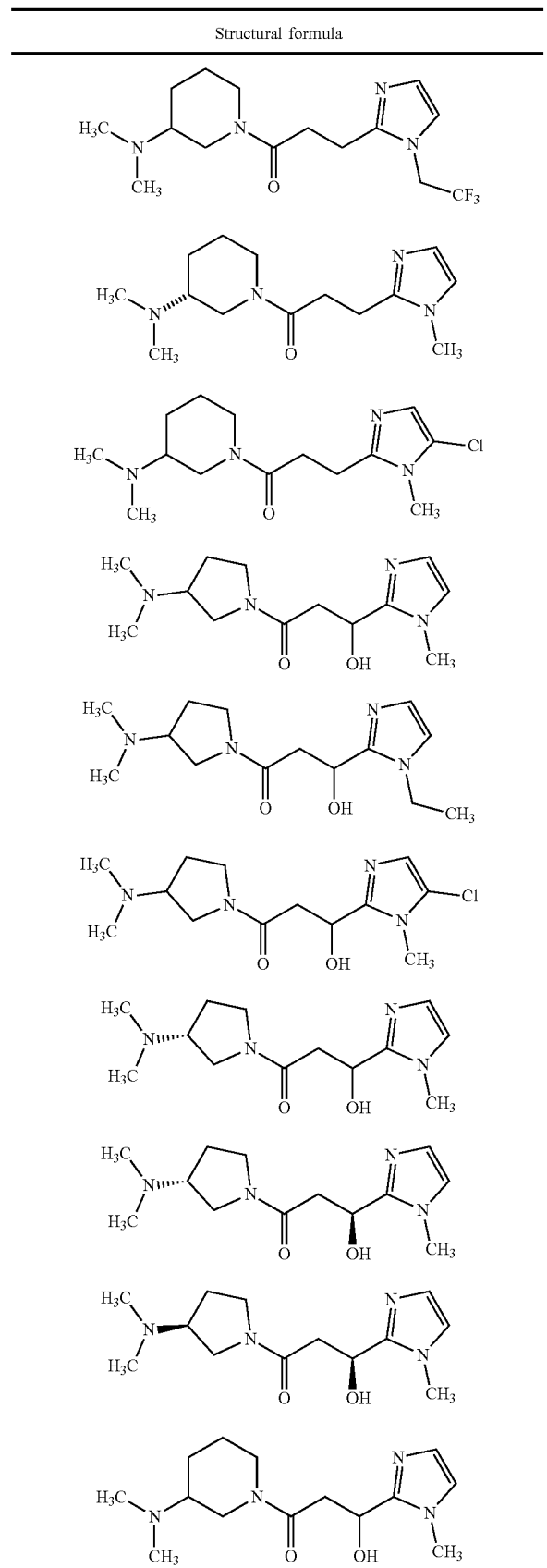

TABLE 1-3-continued

Structural formula

When the cyclic amine derivative (I) has an isomer such as an enantiomer and a stereoisomer, any one of isomers and mixtures of them are included in the cyclic amine derivative (I). In addition, when the cyclic amine derivative (I) has an isomer such as an enantiomer and a stereoisomer, the cyclic amine derivative (I) may be a mixture comprising any one of isomers or a mixture of them. In addition, when the cyclic amine derivative (I) has conformational isomers, the cyclic amine derivative (I) includes any one of isomers and mixtures of them. A desired isomer can be obtained by a known method or a similar method thereto. For example, when an enantiomer of the cyclic amine derivative (I) is present, the enantiomer separated from the cyclic amine derivative (I) is also included in the cyclic amine derivative (I).

A desired enantiomer can be obtained by a known means (for example, an optically active synthetic intermediate is used or final-product racemic mixture is subjected to a known method or a similar method thereto (for example, optical resolution)).

A prodrug of a cyclic amine derivative (I) or a pharmacologically acceptable salt thereof is also included. The prodrug of the cyclic amine derivative (I) refers to a compound, which is enzymatically or chemically converted to the cyclic amine derivative (I) in vivo. The active form of a prodrug of the cyclic amine derivative (I) is the cyclic amine derivative (I). However, a prodrug of the cyclic amine derivative (I) itself may have activity.

As the prodrug of the cyclic amine derivative (I), for example, a compound obtained by alkylation, phosphorylation or boration of a hydroxyl group of the cyclic amine derivative (I) can be mentioned. These compounds can be each synthesized from the cyclic amine derivative (I) in accordance with a known method.

A prodrug of the cyclic amine derivative (I) may be converted into the cyclic amine derivative (I) in physiological conditions described in known literatures ("Development of pharmaceutical products", Hirokawa-Shoten Ltd., vol. 7, p. 163 to 198, 1990, and Progress in Medicine, vol. 5, p. 2157 to 2161, 1985).

The cyclic amine derivative (I) may be labeled with a radioisotope. Examples of radioisotopes for use in labeling include $^2H$, $^3H$, $^{13}C$, $^{14}C$, $^{15}N$, $^{15}O$ and/or 180.

As the pharmacologically acceptable salt of the cyclic amine derivative (I), for example, an inorganic salt such as a hydrochloride, a sulfate, a phosphate and a hydrobromide; or organic salt such as an oxalate, a malonate, a citrate, a fumarate, a lactate, a malate, a succinate, a tartrate, an acetate, a trifluoroacetate, a maleate, a gluconate, a benzoate, a salicylate, a xinafoate, a pamoate, an ascorbate, an adipate, a methanesulfonate, a p-toluenesulfonate and a cinnamate can be mentioned.

The cyclic amine derivative (I) or a pharmacologically acceptable salt thereof includes a hydrate and a solvate thereof.

When the cyclic amine derivative (I) or a pharmacologically acceptable salt thereof has crystalline polymorphs, the cyclic amine derivative (I) or the pharmacologically acceptable salt thereof includes all crystalline polymorphs and mixtures of them.

The cyclic amine derivative (I) or a pharmacologically acceptable salt thereof can be synthesized in accordance with a method described in the known literature (International Publication No. WO 2013/147160) or a known literature (International Publication No. WO 2016/136944), for example.

The term "rise in intracellular calcium concentration" means that the intracellular calcium concentration rises to an extent that abnormal excitatory transmission of neurons occurs, and is indicated by, for example, an intracellular calcium concentration beyond a normal range, the length of a duration of a rise in intracellular calcium concentration beyond a normal range, or the number of rises in intracellular calcium concentration per unit time beyond a normal range, as an index.

The term "inhibition of a rise in intracellular calcium concentration" means that abnormal excitatory transmission of neurons that has occurred is inhibited, or a state without abnormal excitatory transmission of neurons is maintained, and is indicated by, for example, an intracellular calcium concentration within a normal range, the length of a duration of a rise in intracellular calcium concentration within a normal range, or the number of rises in intracellular calcium concentration per unit time within a normal range, as an index. The term "inhibition of a rise in intracellular calcium concentration" also means that the rise in intracellular calcium concentration is inhibited by 10% or more, 20% or more, 30% or more, 40% or more, 50% or more, 60% or more, 70% or more, 80% or more, 90% or more or 100% as compared to when the rise in intracellular calcium concentration is not inhibited.

Examples of the aforementioned disease related to neuronal hyperexcitability include, but are not limited to: central nervous diseases such as Alzheimer's disease, Parkinson's disease, Huntington's disease, Creutzfeldt-Jakob disease, amyotrophic lateral sclerosis (ALS), spinocerebellar degeneration, spinocerebellar ataxia, Down syndrome, multiple sclerosis, schizophrenia, depression, mania, anxiety neurosis, obsessive-compulsive disorder, panic disorder, bipolar disorder, corticobasal degeneration, progressive supranuclear palsy, Lewy body dementia, frontotemporal lobar degeneration, mild cognitive impairment which is a pre-lesion of Alzheimer's disease, frontotemporal lobar dementia, epilepsy, alcoholism, drug addiction, anxiety symptoms, unpleasant mental states, dysthymia, cyclothymia, nervous erethism, autism, fainting, addition and loss of sexual desire; central nervous system or peripheral nervous damages such as head trauma, spinal cord injury, cerebral edema, perceptual dysfunction, diabetic neuropathy, autonomic nervous system dysfunction and whiplash; disorders of memory such as senile dementia, cerebrovascular dementia and amnesia, intracerebral hemorrhage, cerebral infarction and sequelae and complications thereof, cerebrovascular disorders such as asymptomatic cerebrovascular disorder, transient ischemic attack, hypertensive encephalopathy and brain-blood barrier disorder, and recurrence or sequelae of cerebrovascular disorders; decline in central functions after cerebrovascular occlusion and disorder or abnormality of brain or kidney circulation autoregulation; metabolic disorder syndromes such as idiopathic normal pressure hydrocephalus, obstructive hydrocephalus and infectious or metabolic encephalopathy; autoimmune diseases such as optic neuromyelitis and limbic encephalitis; oncological diseases such as neuroepithelial tissue tumors (glioma, neuronal tumor and the like), neurilemmal tumors (neurilemoma, neurofibromatosis and the like), meningeal tumors (meningioma and other mesenchymal tumors), sellar tumor and metastatic tumor; sleep disorder; and pruritus.

The cyclic amine derivative (I) or a pharmacologically acceptable salt thereof can be used as a medicine for treating or preventing a disease related to neuronal hyperexcitability in a mammal (for example, mouse, rat, hamster, rabbit, cat, dog, cow, sheep, monkey or human), and especially to a human.

When the cyclic amine derivative (I) or a pharmacologically acceptable salt thereof is used as a medicine, the cyclic amine derivative (I) or a pharmacologically acceptable salt thereof directly or in combination with a pharmaceutically acceptable carrier can be orally or parenterally administered.

As the dosage form when a medicine containing the cyclic amine derivative (I) or a pharmacologically acceptable salt thereof as an active ingredient is orally administered, for example, tablets (including sugar-coated and film-coated tablets), pills, granules, powders, capsules (including soft capsules and micro capsules), syrups, emulsions and suspensions can be mentioned. As the dosage form when a medicine containing the cyclic amine derivative (I) or a pharmacologically acceptable salt thereof as an active ingredient is parenterally administered, for example, injections, infusions, drops, suppositories, endermic liniments and adhesive patches can be mentioned. It is further effective to prepare a sustained-release formulation by using the cyclic amine derivative (I) or a pharmacologically acceptable salt thereof in combination with an appropriate base (for example, a butyric acid polymer, a glycolic acid polymer, a butyric acid-glycolic acid copolymer, mixtures of a butyric acid polymer and a glycolic acid polymer, or a polyglycerol fatty acid ester).

Formulations having the aforementioned dosage forms can be prepared in accordance with production methods known in the field of drug formulation. In this example, if necessary, production can be made by adding an excipient, a binder, a lubricant, a disintegrating agent, a sweetening agent, a surfactant, a suspending agent or an emulsifying agent, which is generally used in the field of drug formulation.

Tablets can be prepared, for example, by adding an excipient, a binder, a disintegrating agent or a lubricant. Pills and granules can be prepared by adding, for example, an excipient, a binder or a disintegrating agent. Powders and capsules can be prepared by adding, for example, an excipient. Syrups can be prepared by adding, for example, a sweetening agent. Emulsions or suspensions can be prepared by adding, for example, a surfactant, a suspending agent or an emulsifier.

As the excipient, for example, lactose, glucose, starch, sucrose, microcrystalline cellulose, powdered glycyrrhiza, mannitol, sodium hydrogen carbonate, calcium phosphate and calcium sulfate can be mentioned.

As the binder, for example, a starch paste solution, a gum arabic solution, a gelatin solution, a tragacanth solution, a carboxymethylcellulose solution, a sodium alginate solution and glycerin can be mentioned.

As the disintegrating agent, for example, starch and calcium carbonate can be mentioned.

As the lubricant, for example, magnesium stearate, stearic acid, calcium stearate and purified talc can be mentioned.

As the sweetening agent, for example, glucose, fructose, invert sugar, sorbitol, xylitol, glycerin and simple syrup can be mentioned.

As the surfactant, for example, sodium lauryl sulfate, polysorbate 80, sorbitan monofatty acid ester and stearic acid polyoxyl 40 can be mentioned.

As the suspending agent, for example, Gum arabic, sodium alginate, sodium carboxymethylcellulose, methyl cellulose and bentonite can be mentioned.

As the emulsifier, for example, Gum arabic, tragacanth, gelatin and polysorbate 80 can be mentioned.

When a medicine comprising the cyclic amine derivative (I) or a pharmacologically acceptable salt thereof as an active ingredient is prepared in the aforementioned dosage forms, a coloring agent, a preserving agent, a fragrance, a flavoring agent, a stabilizer or a thickener generally used in the field of drug formulation can be added.

The dose per day of a medicine containing the cyclic amine derivative (I) or a pharmacologically acceptable salt thereof as an active ingredient varies depending upon e.g., the state or body weight of the patient or the type or administration route of a compound. For example, in oral administration to an adult (weight: about 60 kg), the amount of the cyclic amine derivative (I) or a pharmacologically acceptable salt thereof serving as an active ingredient falls within the range of 1 to 1000 mg and administration is preferably made in 1 to 3 divided doses. For example, in parenteral administration to an adult (weight: about 60 kg), the amount of the cyclic amine derivative (I) or a pharmacologically acceptable salt thereof serving as an active ingredient falls within the range of 0.01 to 100 mg per body weight (1 kg), and the injectable solution is preferably intravenous administered.

The cyclic amine derivative (I) or a pharmacologically acceptable salt thereof may be blended with other medicinal agents in an appropriate ratio or used in combination with other medicinal agents to supplement or enhance a therapeutic or prophylactic effect or reduce the dose. The cyclic amine derivative (I) or a pharmacologically acceptable salt thereof may be administered concurrently with other medicinal agents or may be administered continuously therewith in an arbitrary order. As the other medicinal agents, for example, but are not limited to, therapeutic agents for the aforementioned disease related to neuronal hyperexcitability can be mentioned. Examples thereof include donepezil, memantine, galantamine, rivastigmine, entacapone, levodopa, benserazide hydrochloride, carbidopa, zonisamide, amantadine hydrochloride, bromocriptine mesylate, pergolide mesylate, cabergoline, pramipexole hydrochloride hydrate, rotigotine, talipexole hydrochloride, ropinirole hydrochloride, apomorphine hydrochloride hydrate, selegiline hydrochloride, trihexyphenidyl hydrochloride, biperiden hydrochloride, promethazine hydrochloride, istradefylline, droxidopa, riluzole, protirelin tartrate hydrate, taltirelin hydrate, chlorpromazine, haloperidol, sulpiride, risperidone, perospirone, olanzapine, quetiapine, paroxetine, fluvoxamine, sertraline, escitalopram, milnacipran, duloxetine, mirtazapine, amoxapine, amitriptyline, imipramine, clomipramine, dosulepin, trimipramine, nortriptyline, lofepramine, setiptiline, maprotiline, mianserin, lithium carbonate, carbamazepine, sodium valproate, lamotrigine, tofisopam, clotiazepam, etizolam, lorazepam, alprazolam, bromazepam, diazepam, clonazepam, cloxazolam, ethyl loflazepate, flutoprazepam, tandospirone citrate, disulfiram, cyanamide, acamprosate, valproic acid, ethosuximide, phenobarbital, carbamazepam, phenytoin, ambenonium chloride, edrophonium chloride, acetylcholine chloride, neostigmine bromide, sugammadex sodium, neostigmine methyl sulfate, piracetam, pyridostigmine bromide, bethanechol chloride, neostigmine methyl sulfate, atropine sulfate hydrate, pregabalin, epalrestat, mexiletine, aspirin, ticlopidine hydrochloride, clopidogrel sulfate, cilostazol, warfarin potassium, dabigatran etexilate methanesulfonate, edoxaban tosylate hydrate, rivaroxaban, apixaban, amobarbital, eszopiclone, estazolam, quazepam, suvorexant, secobarbital sodium, zopiclone, zolpidem tartrate, dexmedetomidine hydrochloride, triazolam, triclofos sodium, nitrazepam, haloxazolam, phenobarbital sodium, flunitrazepam, flurazepam hydrochloride, brotizolam, bromovalerylurea, pentobarbital calcium, chloral hydrate, midazolam, ramelteon, rilmazafone hydrochloride, lormetazepam and nalfurafine hydrochloride.

EXAMPLES

Hereinafter, our agents, compositions and methods will be described in detail below with reference to Examples. However, this disclosure is not limited to them.

The test compounds used were 1-(4-(dimethylamino)piperidin-1-yl)-3-(1-ethyl-1H-imidazol-2-yl)-3-hydroxypropan-1-one (hereinafter, "compound 1"), (S)-1-(4-(dimethylamino)piperidin-1-yl)-3-hydroxy-3-(1-methyl-1H-imidazol-2-yl)propan-1-one (hereinafter, "compound 2"), 1-(4-(dimethylamino)piperidin-1-yl)-3-hydroxy-3-(1-(2,2,2-trifluoroethyl)-1H-imidazol-2-yl)propan-1-one (hereinafter, "compound 3") and 1-(4-(dimethylamino)piperidin-1-yl)-3-(1-methyl-1H-imidazol-2-yl)propan-1-onesulfatemonohydrate (hereinafter, "compound 4") shown in Table 2, and were synthesized according to the methods described in known literatures (International Publication Nos. WO 2013/147160 and WO 2016/136944).

TABLE 2

| Compound No. | Structural formula |
|---|---|
| Compound 1 | (structure) |
| Compound 2 | (structure) |
| Compound 3 | (structure) |
| Compound 4 | (structure) •H$_2$SO$_4$ •H$_2$O |

Further, the test compounds used were 1-((R)-3-(3-(dimethylamino)piperidin-1-yl)-3-hydroxy-3-(1-methyl-1H-imidazol-2-yl)propan-1-one (hereinafter, "compound 5"), 3-hydroxy-3-(1-methyl-1H-imidazol-2-yl)-1-(4-(4-methylpipzerazin-1-yl)piperidin-1-yl)propan-1-one (hereinafter, "compound 6"), 1-(4-(dimethylamino)piperidin-1-yl)-3-(1-propyl-1H-imidazol-2-yl)-3-hydroxypropan-1-one (hereinafter, "compound 7"), 1-((R)-3-(dimethylamino)pyrrolidin-1-yl)-3-hydroxy-3-(1-methyl-1H-imidazol-2-yl)propan-1-one (hereinafter, "compound 8"), 3-(5-chloro-1-methyl-1H-imidazol-2-yl)-1-(4-(dimethylamino)piperidin-1-yl)-3-hydroxypropan-1-one (hereinafter, "compound 9"), 1-(4-(dimethylamino)piperidin-1-yl)-3-(1-isopropyl-1H-imidazol-2-yl)-3-hydroxypropan-1-one (hereinafter, "compound 10"), 1-(4-(dimethylamino)piperidin-1-yl)-3-(1-(2-methoxyethyl)-1H-imidazol-2-yl)-3-hydroxypropan-1-one (hereinafter, "compound of Comparative Example 1") and 1-(4-(dimethylamino)piperidin-1-yl)-3-(1-(3,3,3-trifluoropropyl)-1H-imidazol-2-yl)-3-hydroxypropan-1-one (hereinafter, "compound of Comparative Example 2") shown in Table 3.

Among the test compounds shown in Table 3, compound 5, compound 6 and compound 8 were synthesized according to the methods described in known literatures (International Publication Nos. WO 2013/147160 and WO 2016/136944). Compound 7, compound 9 and compound 10 were synthesized by the methods described in Examples given below. The compounds of Comparative Example 1 and Comparative Example 2 were synthesized by the methods described in Reference Examples given below. Their raw materials and intermediates were synthesized by the methods described in Reference Examples given below. Note that commercially-available products were used for the compounds which were used in synthesizing the compounds of Reference Examples and whose synthesis methods are not described below.

In the following description, the names of the solvents shown in the NMR data represent the solvents used in the measurement. The 400 MHz NMR spectra were measured by using JNM-AL 400 series Nuclear Magnetic Resonance (NMR) spectrometer (JEOL, Ltd.). Chemical shifts are expressed by δ (unit: ppm) using tetramethylsilane as the reference, and the respective signals, respectively have the following meanings: s (singlet), d (doublet), t (triplet), q (quartet), quint (quintet), sept (septet), m (multiplet), br (broad), dd (double doublet), dt (double triplet), ddd (double double doublet), dq (double quartet), td (triple doublet), and tt (triple triplet). The ESI-MS spectra were measured by using Agilent Technologies 1200 Series, G6130A (from Agilent Technology). Commercially available products were used for all the solvents. For flash column chromatography, YFLC W-prep2XY (from YAMAZEN) was used.

Reference Example 1 Synthesis of
1-propyl-1H-imidazole-2-carbaldehyde

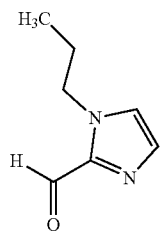

1-Iodopropane (1.22 mL, 12.5 mmol) and potassium carbonate (2.16 g, 15.6 mmol) were added to a solution of 1H-imidazole-2-carbaldehyde (1.00 g, 10.4 mmol) in N,N-dimethylformamide (10.0 mL), and the reaction liquid was stirred at 60° C. for 3 hours. Water was added to the reaction liquid and then the reaction liquid was extracted with ethyl acetate. The organic layer was washed with a 10% aqueous solution of sodium chloride, and then dried over anhydrous sodium sulfate and filtered. The filtrate was concentrated under reduced pressure. The residue was purified by flash column chromatography (silica gel, hexane/ethyl acetate) to obtain 1-propyl-1H-imidazole-2-carbaldehyde (0.786 g, 5.69 mmol, 55%) as a yellow oil.

$^1$H-NMR (400 MHz, CDCl$_3$) δ: 0.93 (3H, t, J=7.4 Hz), 1.77-1.85 (2H, m), 4.37 (2H, t, J=7.2 Hz), 7.16 (1H, s), 7.28 (1H, s), 9.82 (1H, s).

Reference Example 2 Synthesis of
5-chloro-1-methyl-H-imidazole-2-carbaldehyde

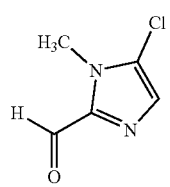

Dess-Martin reagent (1.04 g, 2.46 mmol) was added to a solution of (5-chloro-1-methyl-1H-imidazol-2-yl)methanol (0.300 g, 2.05 mmol) in dichloromethane (20.0 mL) at 0° C. and the reaction liquid was stirred at the same temperature for 3 hours. A 10% aqueous solution of sodium thiosulfate and a saturated aqueous solution of sodium hydrogencarbonate were added to the reaction liquid and then the reaction liquid was extracted with chloroform. The organic layer was washed with a 10% aqueous solution of sodium chloride, and then dried over anhydrous sodium sulfate and filtered. The filtrate was concentrated under reduced pressure. The residue was purified by flash column chromatography (silica gel, hexane/ethyl acetate) to obtain 5-chloro-1-methyl-1H-imidazole-2-carbaldehyde (0.235 g, 1.62 mmol, 79%) as a white solid.

$^1$H-NMR (400 MHz, CDCl$_3$) δ: 3.98 (3H, s), 7.24 (1H, s), 9.70 (1H, s).

Reference Example 3 Synthesis of
1-isopropyl-1H-imidazole-2-carbaldehyde

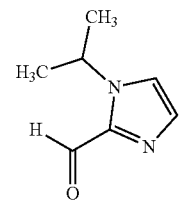

2-Iodopropane (1.26 mL, 12.5 mmol) and potassium carbonate (2.16 g, 15.6 mmol) were added to a solution of 1H-imidazole-2-carbaldehyde (1.00 g, 10.4 mmol) in N,N-dimethylformamide (10 mL) and the reaction liquid was stirred at 60° C. for 3 hours. Water was added to the reaction liquid and then the reaction liquid was extracted with ethyl acetate. The organic layer was washed with a 10% aqueous solution of sodium chloride, and then dried over anhydrous sodium sulfate and filtered. The filtrate was concentrated under reduced pressure. The residue was purified by flash column chromatography (silica gel, hexane/ethyl acetate) to obtain 1-isopropyl-1H-imidazole-2-carbaldehyde (0.703 g, 5.09 mmol, 49%) as a yellow oil.

$^1$H-NMR (400 MHz, CDCl$_3$) δ: 1.47 (6H, t, J=6.6 Hz), 5.48 (1H, q, J=6.6 Hz), 7.30 (1H, s), 7.33 (1H, s), 9.83 (1H, s).

Reference Example 4 Synthesis of
1-(2-methoxyethyl)-1H-imidazole-2-carbaldehyde

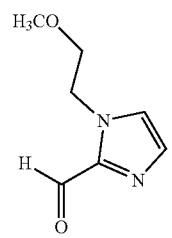

2-Bromoethyl methyl ether (1.20 mL, 12.5 mmol), potassium carbonate (2.16 g, 15.6 mmol), and sodium iodide (0.468 g, 3.12 mmol) were added to a solution of 1H-imidazole-2-carbaldehyde (1.00 g, 10.4 mmol) in N,N-dimethylformamide (10.0 mL) and the reaction liquid was stirred at 60° C. for 3 hours. Water was added to the reaction liquid and then the reaction liquid was extracted with ethyl acetate. The organic layer was washed with a 10% aqueous solution of sodium chloride, and then dried over anhydrous sodium sulfate and filtered. The filtrate was concentrated under reduced pressure. The residue was purified by flash column chromatography (silica gel, hexane/ethyl acetate) to obtain 1-(2-methoxyethyl)-1H-imidazole-2-carbaldehyde (0.535 g, 3.47 mmol, 33%) as a white solid.

1H-NMR (400 MHz, CDCl$_3$) δ: 3.32 (3H, s), 3.67 (2H, t, J=5.0 Hz), 4.59 (2H, t, J=5.0 Hz), 7.23-7.30 (2H, m), 9.81 (1H, s).

Reference Example 5 Synthesis of 1-(3,3,3-trifluoropropyl)-1H-imidazole-2-carbaldehyde

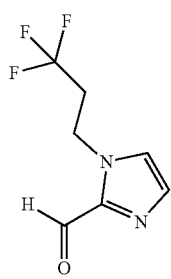 [SMILES: O=Cc1nccn1CCC(F)(F)F]

1,1,1-Trifluoro-3-iodopropane (0.710 mL, 6.24 mmol) and potassium carbonate (1.08 g, 7.81 mmol) were added to a solution of 1H-imidazole-2-carbaldehyde (0.500 g, 5.20 mmol) in N,N-dimethylformamide (5.20 mL) and the reaction liquid was stirred at 60° C. for 5 hours. Water was added to the reaction liquid and then the reaction liquid was extracted with ethyl acetate. The organic layer was washed with a 10% aqueous solution of sodium chloride, and then dried over anhydrous sodium sulfate and filtered. The filtrate was concentrated under reduced pressure. The residue was purified by flash column chromatography (silica gel, hexane/ethyl acetate) to obtain 1-(3,3,3-trifluoropropyl)-1H-imidazole-2-carbaldehyde (0.0863 g, 0.449 mmol, 8.6%) as a colorless oil.

1H-NMR (400 MHz, CDCl$_3$) δ: 2.60-2.72 (2H, m), 4.61 (2H, t, J=6.8 Hz), 7.18 (1H, s), 7.32 (1H, s), 9.83 (1H, s).

Reference Example 6 Synthesis of Compound of Comparative Example 1

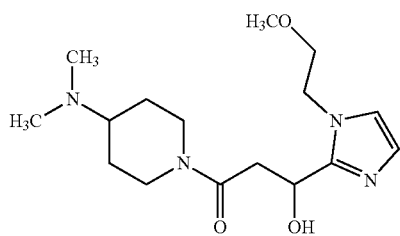

A solution of lithium diisopropylamide in tetrahydrofuran (2.0 M, 0.969 mL, 1.94 mmol) was added dropwise to a solution of 1-(4-dimethylaminopiperidin-1-yl)ethanone (0.300 g, 1.76 mmol) in tetrahydrofuran (6.00 mL) at −78° C. and the reaction liquid was stirred at the same temperature for 1 hour. A solution of 1-(2-methoxyethyl)-1H-imidazole-2-carbaldehyde (0.292 g, 2.12 mmol) in tetrahydrofuran (2.80 mL) was added to the reaction liquid at the same temperature. The reaction liquid was stirred for 1 hour and stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain the compound of Comparative Example 1 (0.193 g, 0.594 mmol, 34%) as a colorless oil.

1H-NMR (400 MHz, DMSO-d6) δ: 1.04-1.40 (2H, m), 1.62-1.80 (2H, m), 2.10-2.35 (7H, m), 2.46-2.59 (1H, m), 2.80-2.90 (1H, m), 2.95-3.10 (2H, m), 3.24 (3H, s), 3.61 (2H, t, J=5.5 Hz), 3.90-4.00 (1H, m), 4.10-4.38 (3H, m), 5.05-5.11 (1H, m), 5.38-5.42 (1H, m), 6.73 (1H, s), 7.07 (1H, s).

Reference Example 7 Synthesis of Compound of Comparative Example 2

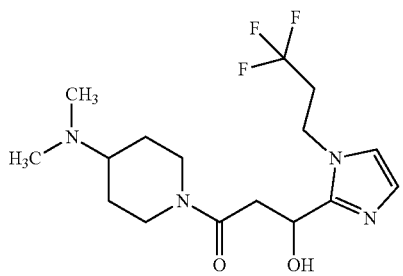 [SMILES: CN(C)C1CCN(C(=O)CC(O)c2nccn2CCC(F)(F)F)CC1]

A solution of lithium diisopropylamide in tetrahydrofuran (2.0 M, 0.246 mL, 0.492 mmol) was added dropwise to a solution of 1-(4-dimethylaminopiperidin-1-yl)ethanone (0.0760 g, 0.448 mmol) in tetrahydrofuran (1.80 mL) at −78° C. and the reaction liquid was stirred at the same temperature for 1 hour. A solution of 1-(3,3,3-trifluoropropyl)-1H-imidazole-2-carbaldehyde (0.0860 g, 0.448 mmol) in tetrahydrofuran (0.70 mL) was added to the reaction liquid at the same temperature. The reaction liquid was stirred for 1 hour and stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain the compound of Comparative Example 2 (0.0845 g, 0.233 mmol, 52%) as a colorless oil.

1H-NMR (400 MHz, DMSO-d6) δ: 1.03-1.40 (2H, m), 1.63-1.79 (2H, m), 2.10-2.33 (7H, m), 2.47-2.59 (1H, m), 2.78-2.90 (3H, m), 2.95-3.13 (2H, m), 3.90-3.98 (1H, m), 4.21-4.36 (3H, m), 5.03-5.10 (1H, m), 5.49-5.54 (1H, m), 6.77 (1H, s), 7.17 (1H, s).

ESI-MS: m/z=363 (M+H)$^+$.

Example 1 Synthesis of Compound 7

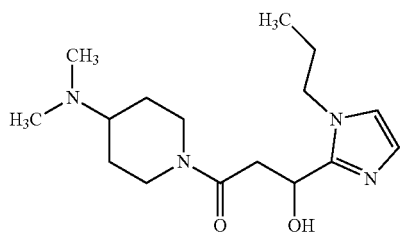 [SMILES: CCCn1ccnc1C(O)CC(=O)N1CCC(N(C)C)CC1]

A solution of lithium diisopropylamide in tetrahydrofuran (2.0 M, 0.969 mL, 1.94 mmol) was added dropwise to a solution of 1-(4-dimethylaminopiperidin-1-yl)ethanone (0.300 g, 1.76 mmol) in tetrahydrofuran (6.00 mL) at −78° C. and the reaction liquid was stirred at the same temperature for 1 hour. A solution of 1-propyl-1H-imidazole-2-carbaldehyde (0.292 g, 2.12 mmol) in tetrahydrofuran (2.8 mL) was added to the reaction liquid at the same temperature. The reaction liquid was stirred for 1 hour and stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain compound 7 (0.296 g, 0.960 mmol, 55%) as a colorless oil.

$^1$H-NMR (400 MHz, DMSO-$d_6$) δ: 0.85 (3H, t, J=7.4 Hz), 1.00-1.40 (2H, m), 1.61-1.80 (4H, m), 2.10-2.33 (7H, m), 2.45-2.59 (1H, m), 2.73-2.88 (1H, m), 2.93-3.13 (2H, m), 3.86-4.00 (3H, m), 4.25-4.35 (1H, m), 4.98-5.05 (1H, m), 5.34-5.40 (1H, m), 6.72 (1H, s), 7.07 (1H, s). ESI-MS: m/z=309 (M+H)$^+$.

Example 2 Synthesis of Compound 9

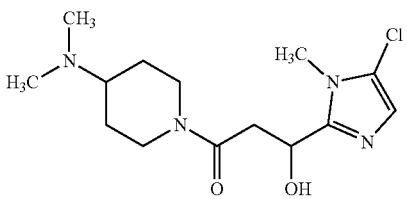 [SMILES: CN(C)C1CCN(C(=O)CC(O)c2ncc(Cl)n2C)CC1]

A solution of lithium diisopropylamide in tetrahydrofuran (2.0 M, 0.745 mL, 1.49 mmol) was added dropwise to a solution of 1-(4-dimethylaminopiperidin-1-yl)ethanone (0.231 g, 1.36 mmol) in tetrahydrofuran (5.10 mL) at −78° C. and the reaction liquid was stirred at the same temperature for 1 hour. A solution of 5-chloro-1-methyl-1H-imidazole-2-carbaldehyde (0.235 g, 1.63 mmol) in tetrahydrofuran (1.70 mL) was added to the reaction liquid at the same temperature, and stirred for 1 hour. The reaction liquid was then stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain compound 9 (0.159 g, 0.505 mmol, 37%) as a colorless oil.

$^1$H-NMR (400 MHz, DMSO-$d_6$) δ: 1.04-1.21 (1H, m), 1.28-1.40 (1H, m), 1.64-1.80 (2H, m), 2.15 (6H, s), 2.24-2.35 (1H, m), 2.44-2.60 (1H, m), 2.78-2.88 (1H, m), 2.95-3.11 (2H, m), 3.59 (3H, s), 3.90-3.98 (1H, m), 4.27-4.35 (1H, m), 5.00-5.10 (1H, m), 5.50-5.58 (1H, m), 6.85 (1H, s). ESI-MS: m/z=315 (M+H)$^+$.

Example 3 Synthesis of Compound 10

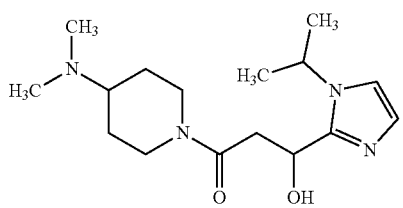 [SMILES: CC(C)n1ccnc1C(O)CC(=O)N1CCC(N(C)C)CC1]

A solution of lithium diisopropylamide in tetrahydrofuran (2.0 M, 0.969 mL, 1.94 mmol) was added dropwise to a solution of 1-(4-dimethylaminopiperidin-1-yl)ethanone (0.300 g, 1.76 mmol) in tetrahydrofuran (6.00 mL) at −78° C. and the reaction liquid was stirred at the same temperature for 1 hour. A solution of 1-isopropyl-1H-imidazole-2-carbaldehyde (0.292 g, 2.12 mmol) in tetrahydrofuran (2.8 mL) was added to the reaction liquid at the same temperature. The reaction liquid was stirred for 1 hour and stirred at 0° C. for further 1 hour. A saturated aqueous solution of ammonium chloride and an aqueous solution of potassium carbonate were sequentially added to the reaction liquid and then the reaction liquid was extracted with chloroform. The organic layer was washed with a 10% aqueous solution of sodium chloride and then dried over anhydrous sodium sulfate and filtered. The filtrate was concentrated under reduced pressure. The residue was purified by flash column chromatography (NH silica gel, chloroform/methanol) to obtain compound 10 (0.302 g, 0.979 mmol, 56%) as a colorless oil.

$^1$H-NMR (400 MHz, DMSO-$d_6$) δ: 1.04-1.41 (8H, m), 1.62-1.80 (2H, m), 2.16 (6H, s), 2.25-2.34 (1H, m), 2.48-2.59 (2H, m), 2.76-2.88 (1H, m), 2.95-3.16 (2H, m), 3.90-4.00 (1H, m), 4.27-4.38 (1H, m), 5.05-5.12 (1H, m), 5.36-5.42 (1H, m), 6.77 (1H, s), 7.20 (1H, s).
ESI-MS: m/z=309 (M+H)$^+$.

TABLE 3

| Compound No. | Structural formula |
|---|---|
| Compound 5 | (structure shown) |

TABLE 3-continued

| Compound No. | Structural formula |
|---|---|
| Compound 6 | [Structure: 4-methylpiperazine-piperidine-C(O)-CH2-CH(OH)-(1-methylimidazol-2-yl)] |
| Compound 7 | [Structure: dimethylamino-piperidine-C(O)-CH2-CH(OH)-(1-ethylimidazol-2-yl)] |
| Compound 8 | [Structure: dimethylamino-cyclopentyl-C(O)-CH2-CH(OH)-(1-methylimidazol-2-yl)] |
| Compound 9 | [Structure: dimethylamino-piperidine-C(O)-CH2-CH(OH)-(1-methyl-5-chloroimidazol-2-yl)] |
| Compound 10 | [Structure: dimethylamino-piperidine-C(O)-CH2-CH(OH)-(1-isopropylimidazol-2-yl)] |
| Compound of Comparative Example 1 | [Structure: dimethylamino-piperidine-C(O)-CH2-CH(OH)-(1-(2-methoxyethyl)imidazol-2-yl)] |
| Compound of Comparative Example 2 | [Structure: dimethylamino-piperidine-C(O)-CH2-CH(OH)-(1-(3,3,3-trifluoropropyl)imidazol-2-yl)] |

Example 4 Effect of the cyclic amine derivative (I) or a pharmacologically acceptable salt thereof on high potassium-induced rise in intracellular calcium concentration of rat spinal dorsal root ganglion (DRG) neurons:

The cyclic amine derivative (I) or a pharmacologically acceptable salt thereof was examined for its inhibitory effect on high potassium-induced rise in intracellular calcium concentration of DRG neurons.

(1) Collection of DRG

The SD rats (4 to 6 weeks old, male; Charles River Laboratories Japan, Inc.) were anesthetized and euthanized by bloodletting from abdominal aorta. After incision of the dorsal part, the spinal column was excised and cooled in ice. The dorsal column was cut off, and the spinal cord was removed from the ventral side of the spinal column. Then, DRGs (L4 to L6) with nerve fibers were excised with tweezers. The excised DRGs were dipped in ice-cold Leibovitz's L-15 medium (Thermo Fisher Scientific), and the nerve fibers were removed under a stereoscopic microscope to separate DRG.

(2) Dissociated Culture of DRG Neurons

The separated DRGs were made fine slits with ophthalmic scissors, followed by incubation at 37° C. for 20 minutes with Collagenase A (Roche Molecular Systems). After centrifugation at 200×g for 5 minutes, the supernatant was removed, and 0.05% Trypsin-EDTA (Thermo Fisher Scientific) was added, followed by incubation at 37° C. for 5 minutes. DMEM (Thermo Fisher Scientific) containing 1% penicillin-streptomycin (Thermo Fisher Scientific) and 10% fetal bovine serum (Thermo Fisher Scientific) was added thereto. After centrifugation at 200×g for 5 minutes, the supernatant was removed. After the removal of the supernatant, Neurobasal-A Medium (Thermo Fisher Scientific) containing 1% penicillin-streptomycin and 2% B-27 (Thermo Fisher Scientific), which was prepared as a DRG nerve culture medium, was added. Then, the cells were dissociated by micropipetting. The dissociated cells were passed through a 70 μm cell strainer (Greiner) and centrifuged at 200×g for 5 minutes. After the centrifugation, the supernatant was removed, and the cells were suspended by the culture medium. This cell suspension was inoculated to a polylysine-coated 35 mm dish (Matsunami Glass Ind., Ltd.) coated in advance with laminin (Sigma-Aldrich), cultured overnight at 37° C. under 5% $CO_2$, and then used in the measurement of change in intracellular calcium concentration.

(3) Loading of Calcium Fluorescent Dye

Cal-520, AM(registered trademark) (AAT Bioquest) was used as a calcium fluorescent dye. The medium was removed from the cells cultured in the dish, and the cells were washed twice with a perfusate. Then, a Cal-520, AM solution adjusted to 4 μmol/L was added thereto, and the cells were cultured at 37° C. for 1 to 1.5 hours under 5% $CO_2$. The perfusate was an aqueous solution containing NaCl (140 mmol/L), KCl (5 mmol/L), $CaCl_2 \cdot 2H_2O$ (1.2 mmol/L), $MgCl_2 \cdot 6H_2O$ (2 mmol/L), D(+)-glucose (14 mmol/L) and HEPES (10 mmol/L), adjusted to pH 7.4. Then, the dish was washed by perfusion at 2 mL/min for 10 minutes.

(4) Measurement of Change in Intracellular Calcium Concentration

Change in intracellular calcium concentration was measured by analyzing with analytical software, change in fluorescence intensity of the cells loaded with the calcium fluorescent dye in images taken under a confocal laser microscope system (Nikon Instech Co., Ltd.). The laser wavelength was 488 nm, and the images were acquired at intervals of 57 to 60 sheets per minute.

For the induction of neuronal excitation, a treatment with a high potassium solution (hereinafter, "high potassium treatment") was performed to induce a rise in intracellular calcium concentration by the depolarization of cell membranes. The high potassium treatment and a treatment with the cyclic amine derivative (I) or a pharmacologically acceptable salt thereof (compounds 1 to 10, compound of Comparative Example 1 and compound of Comparative Example 2) (hereinafter, "compound treatment") of the cells were performed by the perfusion and replacement of a solution. The perfusion rate was controlled to 2 mL/min using a tube pump. The induction of a rise in intracellular calcium concentration by the high potassium treatment was performed by treating the cells for 1 minute using an aqueous solution containing NaCl (125 mmol/L or 115 mmol/L), KCl (32.5 mmol/L or 30 mmol/L), $CaCl_2 \cdot 2H_2O$ (1.2 mmol/L), $MgCl_2 \cdot 6H_2O$ (2 mmol/L), D(+)-glucose (14 mmol/L) and HEPES (10 mmol/L), adjusted to pH 7.4. The high potassium treatment was performed 8 times at 5-minute intervals. Each of the compound 1 to 10, the compound of Comparative Example 1 and the compound of Comparative Example 2 was dissolved at 100 mmol/L in distilled water (Otsuka Pharmaceutical Factory), then diluting the solution into 30 μmol/L with a perfusate, and the compound treatment was performed by treating the cells with the resulting solution. The compound treatment was continuously performed from 3 minutes before the beginning of the third run of the high potassium treatment to after the end of the eighth run of the high potassium treatment (hereinafter, "compound treatment group"). For a control, a treatment using a solution obtained by diluting distilled water with a perfusate was continuously performed from 3 minutes before the beginning of the third run of the high potassium treatment to after the end of the eighth run of the high potassium treatment (hereinafter, "vehicle treatment group"). However, as for the compounds 5 to 10, the compound of Comparative Example 1 and the compound of Comparative Example 2, the induction of a rise in intracellular calcium concentration by the high potassium treatment was performed by treating the cells for 1 minute with an aqueous solution containing NaCl (115 mmol/L), KCl (30 mmol/L), $CaCl_2 \cdot 2H_2O$ (1.2 mmol/L), $MgCl_2 \cdot 6H_2O$ (2 mmol/L), D(+)-glucose (14 mmol/L) and HEPES (10 mmol/L), adjusted to pH 7.4.

(5) Image Analysis and Calculation of Inhibition Rate of Rise in Intracellular Calcium Concentration The taken images were analyzed using ImageJ 1.51j8 (National Institutes of Health). The luminance value of each cell was measured over time to prepare a curve of time-dependent change in luminance value. An area under the curve (AUC) of time-dependent change in luminance value was calculated for each run of the high potassium treatment. The response rate of each cell was calculated as the ratio of total AUC of the seventh and eighth runs of the high potassium treatment to total AUC of the first and second runs of the high potassium treatment according to Expression (1) below. Next, the inhibition rate of a rise in intracellular calcium concentration of each cell was calculated according to Expression (2) below on the basis of the response rate of each cell and an average of response rate of all the cells in the vehicle treatment group. An average of inhibition rate for all the cells in each group was regarded as the inhibition rate for each group, and the inhibition rate of a rise in intracellular calcium concentration for the vehicle treatment group was defined as 0%.

Response rate of each cell=(Total AUC of the seventh and eighth runs of the high potassium treatment)/(Total AUC of the first and second runs of the high potassium treatment)×100     (1)

Inhibition rate of a rise in intracellular calcium concentration of each cell (%)=[1−(Response rate of each cell)/(Average of response rate of all the cells in the vehicle treatment group)]×100     (2)

The inhibitory effects of the compounds 1 to 4 on a rise in intracellular calcium concentration induced by the high potassium treatment of the DRG neurons are shown in Table 4. In the table, "Inhibition rate" represents the calculated inhibition rate of a rise in intracellular calcium concentration (which is an average value; the number of cells in each group was 106 to 262). In the table, "Compound 1", "Compound 2", "Compound 3" and "Compound 4" represent the compound treatment group for each compound. In the table, "#" and "###" indicate statistically significant (#: $p<0.05$, ###: $p<0.001$, Dunnett's multiple comparison test) difference compared to the vehicle treatment group.

TABLE 4

| Test compound | Inhibition rate (%) |
| --- | --- |
| Compound 1 | 35.5### |
| Compound 2 | 19.3### |
| Compound 3 | 17.8### |
| Compound 4 | 11.9# |

In all the compound treatment groups, a rise in intracellular calcium concentration was significantly inhibited, as compared to the vehicle treatment group. This demonstrated that the compounds 1 to 4 inhibit a high potassium-induced rise in intracellular calcium concentration of DRG neurons. The inhibition rate of a rise in intraneuronal calcium concentration in the compound treatment groups using the compounds 1 to 3 of formula (I) wherein $R^1$ is a hydroxyl group was stronger than that in the compound treatment group by the compound 4 of formula (I) wherein $R^1$ is a hydrogen atom.

The inhibitory effects of the compounds 5 to 10, the compound of Comparative Example 1 and the compound of Comparative Example 2 examined in the same way as above are shown in Table 5 (which is an average value; the number of cells in each group was 60 to 250). In the table, "Compound 5", "Compound 6", "Compound 7", "Compound 8", "Compound 9", "Compound 10", "Compound of Comparative Example 1" and "Compound of Comparative Example 2" represent the compound treatment group using each compound. In the table, "###" indicates a statistically significant (###: $p<0.001$, Dunnett's multiple comparison test) difference compared to the vehicle treatment group.

TABLE 5

| Test compound | Inhibition rate (%) |
| --- | --- |
| Compound 5 | 39.0### |
| Compound 6 | 23.3### |
| Compound 7 | 15.4### |
| Compound 8 | 13.2### |
| Compound 9 | 7.1 |
| Compound 10 | 5.9 |
| Compound of Comparative Example 1 | −3.3 |
| Compound of Comparative Example 2 | −1.1 |

In the compound 5 to 10 treatment groups, a rise in intracellular calcium concentration was inhibited. Among them, in the compound 5 to 8 treatment groups, a rise in intracellular calcium concentration was significantly inhibited, as compared to the vehicle treatment group. On the other hand, a rise in intracellular calcium concentration was not inhibited by the compound of Comparative Example 1 and the compound of Comparative Example 2 in their respective treatment groups.

These results demonstrated that the cyclic amine derivative (I) or a pharmacologically acceptable salt thereof serves as an agent for inhibiting a rise in intraneuronal calcium concentration.

INDUSTRIAL APPLICABILITY

The cyclic amine derivative (I) or a pharmacologically acceptable salt thereof remarkably inhibits a rise in intraneuronal calcium concentration and as such, can be used as a medicine for a disease related to neuronal hyperexcitability.

All publications, patents and patent applications cited herein are incorporated herein by reference in their entirety.

The invention claimed is:

1. A method of inhibiting a rise in intraneuronal calcium concentration, comprising administering an effective amount of a cyclic amine derivative represented by formula (I) or a pharmacologically acceptable salt thereof to a subject in need thereof:

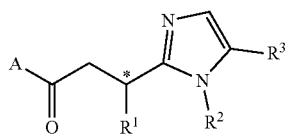

(I)

wherein A represents a group represented by formula (IIa), (IIb) or (IIc):

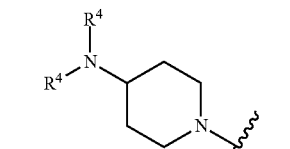

(IIa)

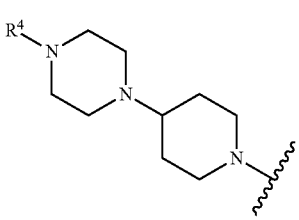

(IIb)

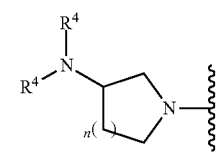

(IIc)

wherein $R^1$ represents a hydroxyl group or a hydrogen atom, $R^2$ represents a methyl group, an ethyl group, a n-propyl group, an isopropyl group, a n-butyl group, a difluoromethyl group or a 2,2,2-trifluoroethyl group, $R^3$ represents a hydrogen atom, a fluorine atom, a bromine atom or a chlorine atom, each $R^4$ independently represents a methyl group or an ethyl group, n represents 1 or 2, and when $R^1$ represents a hydroxyl group, carbon marked with * represents asymmetric carbon.

2. The method according to claim 1, wherein A is represented by formula (IIa).

3. The method according to claim 1, wherein A is represented by formula (IIb).

4. The method according to claim 1, wherein A is represented by formula (IIc).

5. The method according to claim 1, wherein $R^1$ is a hydrogen atom.

6. The method according to claim 1, wherein $R^1$ is a hydroxyl group.

7. The method according to claim 1, wherein $R^2$ is a methyl group, an ethyl group, an isopropyl group, a n-butyl group or a 2,2,2-trifluoroethyl group.

8. The method according to claim 1, wherein $R^2$ is a n-propyl group.

9. The method according to claim 1, wherein $R^3$ is a hydrogen atom or a chlorine atom.

10. The method according to claim 1, wherein a stereochemical configuration of the asymmetric carbon marked with * is S.

11. The method according to claim 1, wherein the cyclic amine derivative represented by formula (I) or the pharmacologically acceptable salt thereof is selected from the group consisting of:

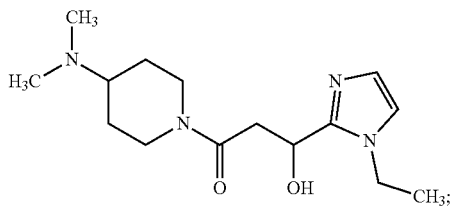

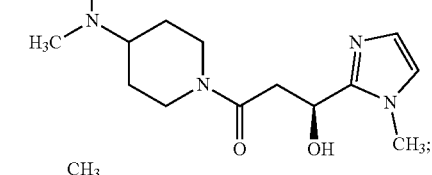

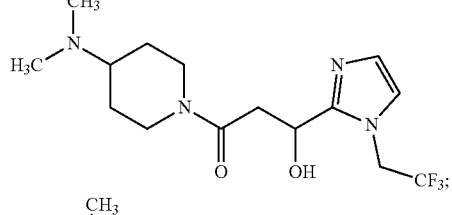

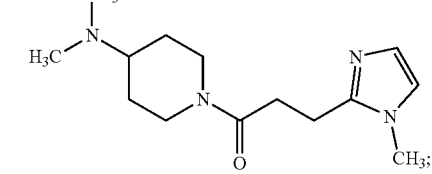

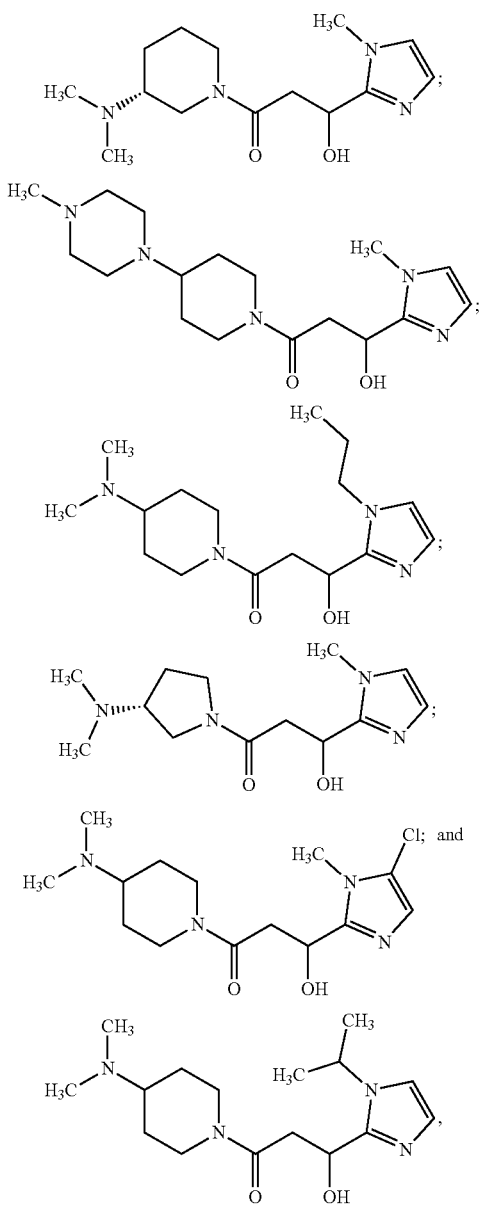

and a pharmacologically acceptable salt thereof, and a solvate thereof.

12. A method of treating a disease related to neuronal hyperexcitability, comprising administering a therapeutically effective amount of a cyclic amine derivative represented by formula (I) or a pharmacologically acceptable salt thereof to a subject in need thereof:

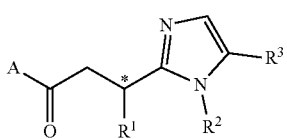
(I)

wherein A represents a group represented by formula (IIa), (IIb) or (IIc):

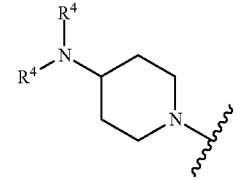
(IIa)

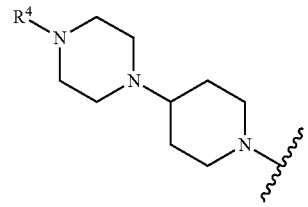
(IIb)

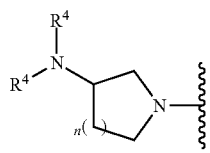
(IIc)

wherein $R^1$ represents a hydroxyl group or a hydrogen atom, $R^2$ represents a methyl group, an ethyl group, a n-propyl group, an isopropyl group, a n-butyl group, a difluoromethyl group or a 2,2,2-trifluoroethyl group, $R^3$ represents a hydrogen atom, a fluorine atom, a bromine atom or a chlorine atom, each $R^4$ independently represents a methyl group or an ethyl group, n represents 1 or 2, and when $R^1$ represents a hydroxyl group, carbon marked with * represents asymmetric carbon.

13. The method according to claim 12, wherein A is represented by formula (IIa).

14. The method according to claim 12, wherein A is represented by formula (IIb).

15. The method according to claim 12, wherein A is represented by formula (IIc).

16. The method according to claim 12, wherein $R^1$ is a hydrogen atom.

17. The method according to claim 12, wherein $R^1$ is a hydroxyl group.

18. The method according to claim 12, wherein $R^2$ is a methyl group, an ethyl group, an isopropyl group, a n-butyl group or a 2,2,2-trifluoroethyl group.

19. The method according to claim 12, wherein $R^2$ is a n-propyl group.

20. The method according to claim 12, wherein $R^3$ is a hydrogen atom or a chlorine atom.

21. The method according to claim 12, wherein a stereochemical configuration of the asymmetric carbon marked with * is S.

22. The method according to claim 12, wherein the disease related to neuronal hyperexcitability is associated with a rise in intraneuronal calcium concentration.

23. The method according to claim 12, wherein the cyclic amine derivative represented by formula (I) or the pharmacologically acceptable salt thereof is selected from the group consisting of:

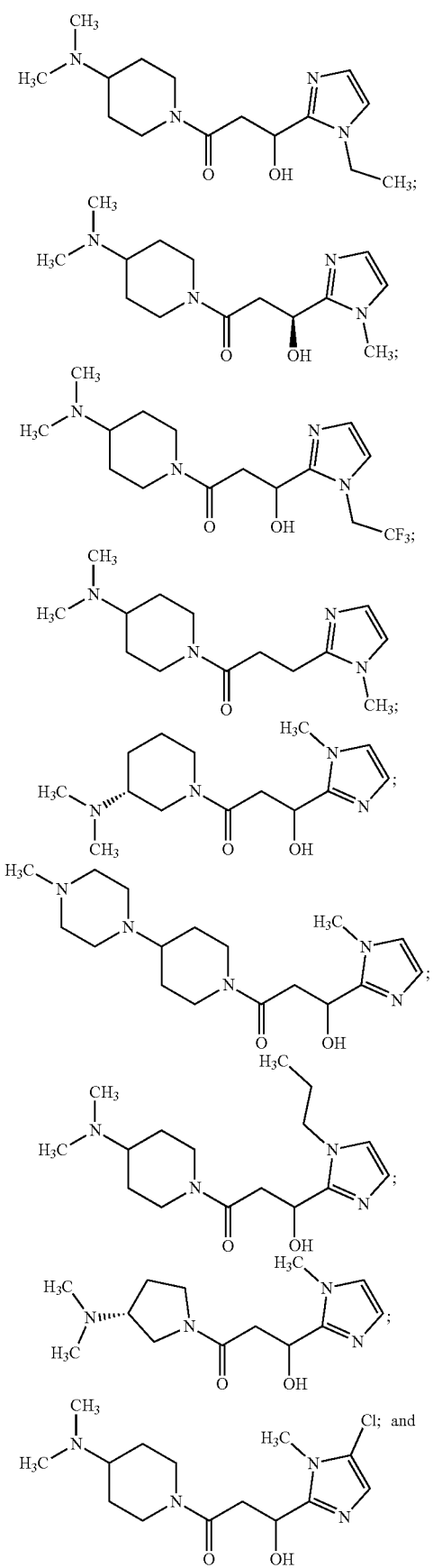

-continued

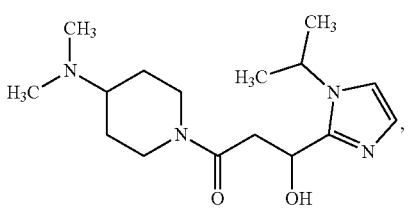

and a pharmacologically acceptable salt thereof, and a solvate thereof.

24. A method of inhibiting a rise in intraneuronal calcium concentration, comprising contacting an effective amount of a cyclic amine derivative represented by formula (I) or a pharmacologically acceptable salt thereof with neurons:

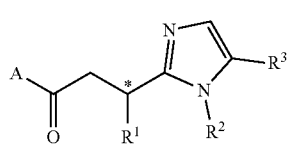
(I)

wherein A represents a group represented by formula (IIa), (IIb) or (IIc):

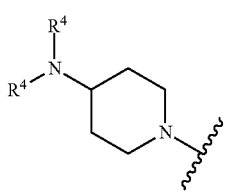
(IIa)

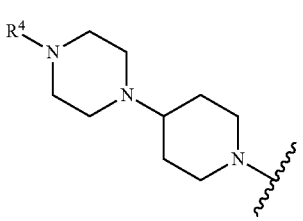
(IIb)

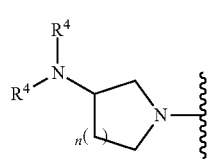
(IIc)

wherein $R^1$ represents a hydroxyl group or a hydrogen atom, $R^2$ represents a methyl group, an ethyl group, a n-propyl group, an isopropyl group, a n-butyl group, a difluoromethyl group or a 2,2,2-trifluoroethyl group, $R^3$ represents a hydrogen atom, a fluorine atom, a bromine atom or a chlorine atom, each $R^4$ independently represents a methyl group or an ethyl group, n represents 1 or 2, and when $R^1$ represents a hydroxyl group, carbon marked with * represents asymmetric carbon.

* * * * *

UNITED STATES PATENT AND TRADEMARK OFFICE
CERTIFICATE OF CORRECTION

PATENT NO. : 11,510,914 B2
APPLICATION NO. : 17/040458
DATED : November 29, 2022
INVENTOR(S) : Serizawa et al.

It is certified that error appears in the above-identified patent and that said Letters Patent is hereby corrected as shown below:

In the Specification

In Column 18
At Line 22, Please change "180" to --$^{18}O$--.

Signed and Sealed this
Twenty-seventh Day of August, 2024

Katherine Kelly Vidal
*Director of the United States Patent and Trademark Office*